United States Patent [19]  [11] 4,409,146
Thorsett et al.  [45] Oct. 11, 1983

[54] SUBSTITUTED CAPROLACTAM DERIVATIVES AS ANTIHYPERTENSIVES

[75] Inventors: Eugene D. Thorsett, Fanwood; Elbert E. Harris, Westfield, both of N.J.

[73] Assignee: Merck & Co., Inc., Rahway, N.J.

[21] Appl. No.: 394,972

[22] Filed: Jul. 2, 1982

Related U.S. Application Data

[63] Continuation-in-part of Ser. No. 294,863, Aug. 25, 1981, abandoned, which is a continuation-in-part of Ser. No. 194,692, Oct. 6, 1980, abandoned.

[51] Int. Cl.³ .......................................... C07D 223/10
[52] U.S. Cl. ............................. 260/239.3 R; 424/244
[58] Field of Search ................ 260/239.3 R; 424/244, 424/273 R, 274

[56] References Cited

U.S. PATENT DOCUMENTS 4,052,511 10/1977 Cushman et al. ................... 424/274

OTHER PUBLICATIONS

Derwent Abstract of German Patent Application 2704-985, U.S. Ser. No. 657,793.
Derwent Abstract of German Patent Application 2704-996, U.S. Ser. No. 684,605.
Derwent Abstract of German Patent Application 2810-261, U.S. Ser. No. 776,793.
Abstract of ACS Meeting of 9/11/78 entitled "Superactive Analogs of the Angiotensin Converting Enzyme Inhibitor BPP$_{9a}$ Containing L-3,4-Dehydroproline".

Primary Examiner—Robert T. Bond
Attorney, Agent, or Firm—Salvatore C. Mitri; Rudolph J. Anderson

[57] ABSTRACT

Substituted caprolactam derivatives are disclosed which are useful as converting enzyme inhibitors and as antihypertensives.

8 Claims, No Drawings

SUBSTITUTED CAPROLACTAM DERIVATIVES AS ANTIHYPERTENSIVES

BACKGROUND OF THE INVENTION

This application is a continuation-in-part of pending application Ser. No. 294,863 filed Aug. 25, 1981, now abandoned which, in turn, is a continuation-in-part of prior application Ser. No. 194,692 filed Oct. 6, 1980, now abandoned.

The invention in its broad aspect relates to caprolactam derivatives which are useful as converting enzyme inhibitors and as antihypertensives. The compounds of this invention can be shown by the following formula:

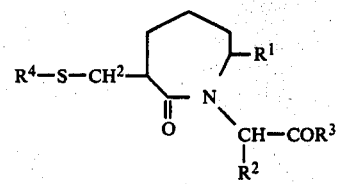

wherein
- $R^1$ is hydrogen, loweralkyl, cyclic loweralkyl, amino loweralkyl, alkylamino loweralkyl, hydroxyalkyl, acylamino loweralkyl, dialkylamino loweralkyl including cyclic polyethyleneamino loweralkyl, arloweralkyl, aryl, substituted aryl wherein the substituent is halo, alkyl, aminoalkyl, or alkoxy; heteroaryl, heteroarloweralkyl;
- $R^2$ is hydrogen or loweralkyl;
- $R^3$ is hydroxyl, loweralkoxy, or aralkyloxy;
- $R^4$ is hydrogen or loweralkanoyl; and, the pharmaceutically acceptable salts thereof.

As used throughout this application, including the claims, and unless specified otherwise:
- alkyl denotes straight and branched hydrocarbons of $C_1$-$C_{12}$ and loweralkyl denotes straight and branched hydrocarbons of $C_1$-$C_8$;
- aryl and the prefix "ar" denote unsubstituted aromatic ring or rings of $C_6$-$C_{12}$ such as, for example, phenyl, naphthyl, biphenyl;
- acyl denotes a carboxylic acid derivative represented by the formula

wherein R is alkane, aralkane, arene, heteroarene, heteroaralkene, and substituted derivatives thereof so that acyl denotes, for example, alkanoyl, aroyl, aralkanoyl, heteroaryl, heteroaralkanoyl, and the like;
- cycloalkyl denotes an unsubstituted alkyl ring of $C_3$-$C_{10}$;
- hetero denotes the heteroatoms, N, O or S;
- heteroaryl denotes an aryl group containing a heteroatom;
- heterocycle denotes a saturated or unsaturated aromatic or non-aromatic cyclic compound containing a heteroatom; and
- halogen and halo denote F, Br, Cl or I atoms.

Preferred are compounds of Formula I wherein
$R^1$ is hydrogen, loweralkyl, aminoloweralkyl, or aryl;
$R^2$ is hydrogen or loweralkyl;
$R^3$ is hydroxyl, or loweralkoxy; and,
$R^4$ is hydrogen or loweralkanoyl.

The preferred compounds of this invention also include the pharmaceutically acceptable salts thereof.

The products of Formula (I) and the preferred subgroup can be produced by one or more of the methods and subroutes depicted in the following equations. The definitions of $R^1$, $R^2$, $R^3$ and $R^4$ are the same as in Formula (I) except where noted.

Method A

3-Carboxyperhydroazepine or a 7-substituted derivative II, prepared by the method of P. Krogsgaard-Larsen et al. [Acta Chem. Scand. B32, 327 (1978)] is converted to the benzyl ester III by known methods. The t-butyl ester could also be used. Alkylation of III with a haloester (X=Br, I) to afford V can be done by known methods, as for example, in a suitable solvent, such as benzene in the presence of silver oxide. Removal of the benzyl group, B, by hydrogenolysis affords the monoester VI. Rearrangement of VI under conditions described by H. Rapoport et al. [J. Org. Chem., 39, 893 (1974)] produces the olefin VII. Reaction of this olefin with a thiol derivative VIII, as, for example, thiolacetic acid, gives I. Groups $R_3$ and $R_4$ may be modified by known methods if desired. For example, if $R_3$=$OCH_3$ and $R_4$=$CH_3CO$, the diester I can be converted to the mercapto acid, ($R_3$=OH, $R_4$=H), by basic hydrolysis.

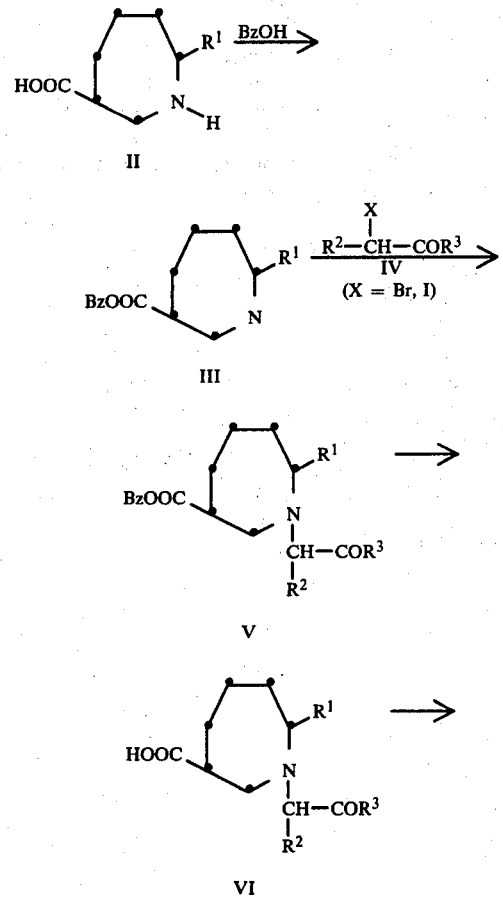

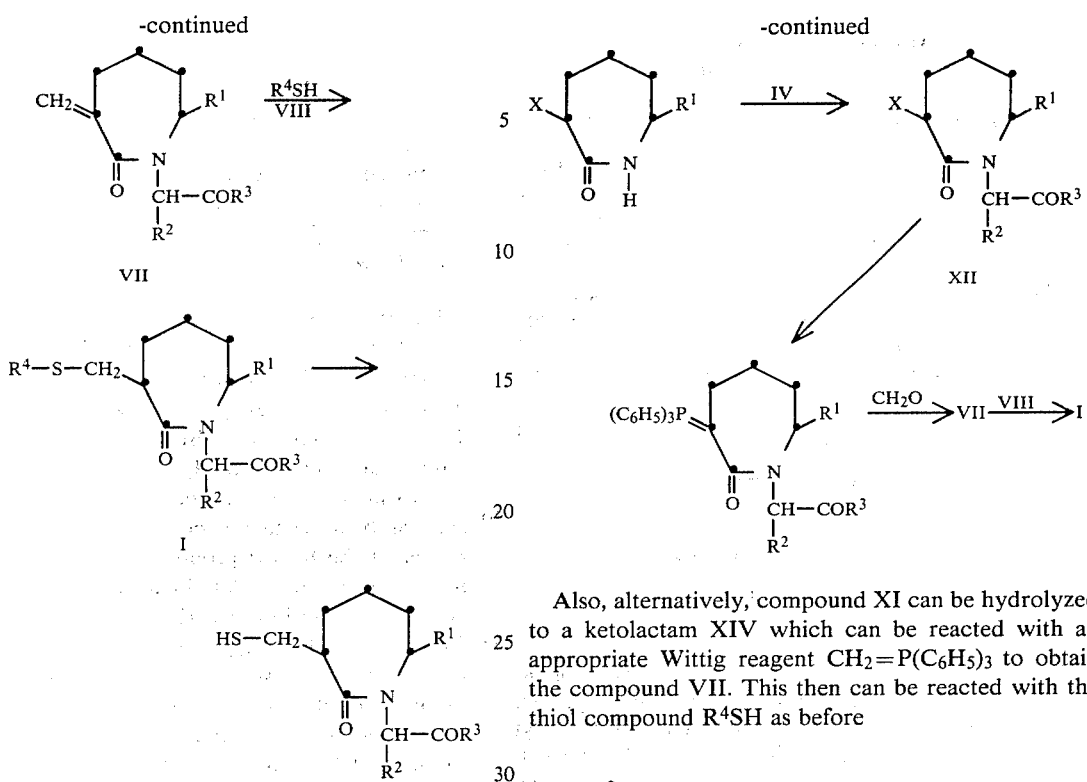

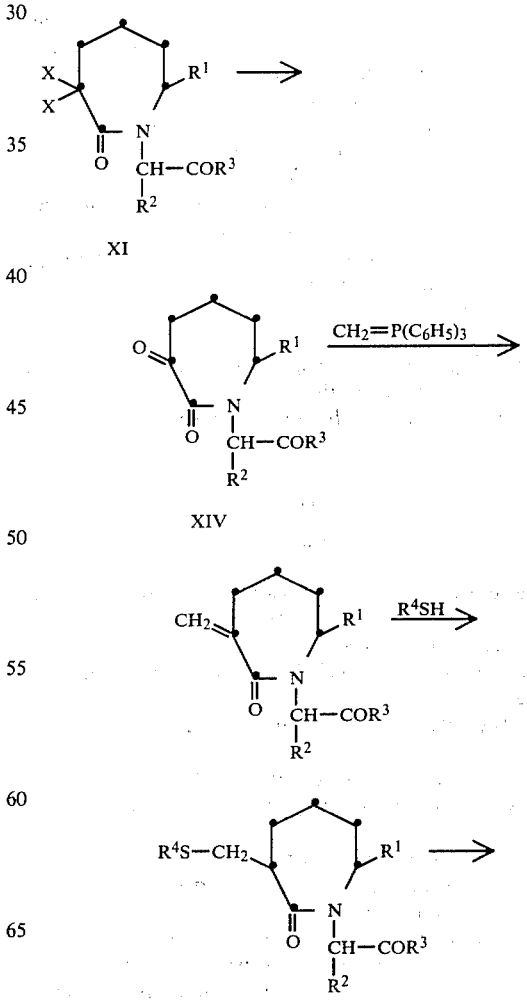

Also, alternatively, compound XI can be hydrolyzed to a ketolactam XIV which can be reacted with an appropriate Wittig reagent $CH_2=P(C_6H_5)_3$ to obtain the compound VII. This then can be reacted with the thiol compound $R^4SH$ as before

Method B

A caprolactam derivative IX, prepared by the method of F. Blicke et al. [J. Am.Chem. Soc. 76, 2317 (1954)], is reacted with $PX_5$, (X=Cl or Br) to obtain compound X [H. Nagasawa et al., J. Med. Chem., 14 501 (1971)]. Reaction of X with haloester IV (X=Br, I) in the presence of a strong base, such as sodium hydride, and in a suitable solvent, such at THF or DMF, affords compound XI. Removal of one halogen can be accomplished by using hydrogen and a suitable catalyst such as palladium on carbon. The monohalide XII can be reacted with a suitable trivalent phosphorus compound, such as triphenylphosphine, followed by a base, such as sodium hydroxide, analogous to the procedure described by G. Howie et al. [J. Med. Chem., 17, 840 (1974)]. The resulting compound XIII is then reacted with an aldehyde, such as formaldehyde, to produce compound VII, which can be converted to I as described in Method A.

Alternatively, compound IX can be converted directly to monohalide XIV [H. Nagasawa et al., above] and alkylated with IV as described under Method A to give XII.

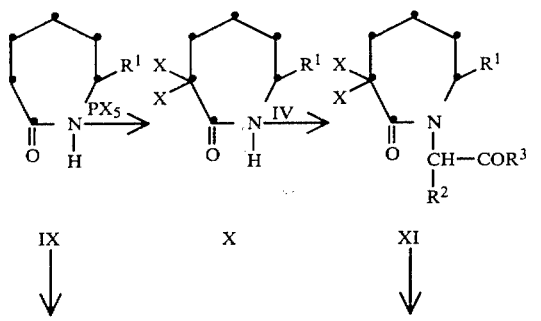

-continued

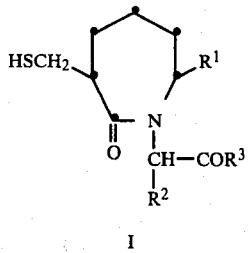

The starting materials which are required for the above processes herein described are known in the literature or can be made by known methods from known starting materials.

In products of general Formula (I), the carbon atoms to which $R^1$ and $R^2$ are attached when these substitutents are not hydrogen and the ring carbon atom to which the fragment

is attached are asymmetric. The compounds accordingly exist in enantiomeric or diastereoisomeric forms or in mixtures thereof. The above described syntheses can utilize racemates or enantiomers as starting materials. When diastereomeric products result from the synthetic procedures, the diastereomeric products can be separated by conventional chromatographic or fractional crystallization methods. When racemic products result, they maybe resolved by crystallization of salts of optically active acids or bases or by other methods known in the art. In general, the aminoacid part-structure,

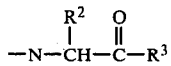

and the ring carbons to which $R^1$ and $R^4$—S—CH$_2$ in Formula (I) compounds can be in two configurations (S or R) and both are herein covered.

The compounds of this invention form salts with various inorganic and organic bases which are also within the scope of the invention. Such salts include ammonium salts, alkali metal salts like sodium and potassium salts, alkaline earth metal salts like the calcium and magnesium salts, salts with organic bases, e.g., dicyclohexylamine, N-methyl-D-glucamine, salts with amino acids like arginine, lysine and the like. The non-toxic physiologically acceptable salts are particularly valuable, although other salts are also useful, e.g., in isolating or purifying the product.

The salts may be formed by conventional means, as by reacting the free acid form of the product with one or more equivalents of the appropriate base in a solvent or medium in which the salt is insoluble, or in a solvent such as water which is then removed *in vacuo* or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., Biochemistry 16, 5484 (1977).

The evaluation of converting enzyme inhibitors is guided by in vitro enzyme inhibition assays. For example, a useful method is that of Y. Piquilloud, A. Reinharz and M. Roth, Biochem. Biophys. Acta, 206, 136 (1970) in which the hydrolysis of carbobenzyloxyphenylalanylhistidinylleucine is measured. *In vivo* evaluations may be made, for example, in normotensive rats challenged with angiotensin I by the technique of J. R. Weeks and J. A. Jones, Proc. Soc. Exp. Biol. Med., 104, 646 (1960) or in a high renin rat model such as that of S. Koletsky et al., Proc. Soc. Exp. Biol. Med., 125, 96 (1967).

Thus, the compounds of this invention are useful an antihypertensives in treating hypertensive mammals, including humans and they can be utilized to achieve the reduction of blood pressure by formulating in compositions such as tablets, capsules or elixirs for oral administration or in sterile solutions or suspensions for parenteral administration. The compounds of this invention can be administered to patients (animals and human) in need of such treatment in a dosage range of 10 to 500 mg per patient generally given several times, thus giving a total daily dose of from 10 to 1500 mg per day. The dose will vary depending on severity of disease, weight of patient and other factors which a person skilled in the art will recognize.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propanolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–100 milligrams per day range can be effectively combined at levels at the 0.5–100 milligrams per day range with the following compounds at the indicated per day dose range: hydrochlorothiazide (10–100 mg), timolol (5–6 mg), methyl dopa (65–2000 mg), the pivaloyloxyethyl ester of methyl dopa (30–1000 mg), indacrinone and variable ratios of its enantiomers (25–150 mg) and (+)-4-{3-{[2-(1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus timolol (5–60 mg) plus converting enzyme inhibitor of this invention (2–1500 mg) of hydrochlorothiazide (10–100 mg) plus amiloride (5–20 mg) plus converting enzyme inhibitor of this invention (2–1500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically the compounds shown above are formulated into pharmaceutical compositions as discussed below.

About 10 to 100 mg. of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; and excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization.

EXAMPLE 1

1-Carboxymethyl-3-mercaptomethylperhydroazepin-2-one

A. 3-Benzyloxycarbonylperhydroazeapine

Suspend 1.15 g of 3-carboxyperhydroazepine [P. Krogsgaard-Larsen et al., Acta Chem. Scand., B32, 327 (1978)] in 8 ml benzyl alcohol. Cool the mixture to 0° and add 1 ml thionyl chloride. Stir the mixture at room temperature for 48 hours, then add it dropwise to 300 ml ether with vigorous stirring. Decant the ether and dissolve the residue in $H_2O$. Wash the aqueous solution with ether, then make it to pH 12 and extract with ethyl acetate. Dry the extracts and concentrate in vacuo to obtain 3-benzyloxycarbonylperhydroazepine.

B. 1-Methoxycarbonylmethyl-3-benzyloxycarbonylperhydroazepine

To a solution of 1.46 g 3-benzyloxycarbonylperhydroazepine and 1.06 g methyl bromoacetate in 30 ml benzene add 1.06 g silver oxide. Stir the reaction in the dark for 24 hr., filter and concentrate the filtrate in vacuo. Dissolve the residue in HCl (pH 1.5) and wash the solution with ether. Make the aqueous phase to pH 12 and extract with ethyl acetate. Dry and concentrate the extracts to obtain 1-methoxycarbonylmethyl-3-benzyloxycarbonylperhydroazepine.

NMR ($CDCl_3$, TMS) $\delta1.8$; (m, 6H); $\delta2.8$ (m, 2H); $\delta3.1$ (d, 2H); $\delta3.45$ (s, 2H); $\delta3.65$ (s, 3H); $\delta5.15$ (s, 2H); $\delta7.3$ (s, 5H).

C. 1-Methoxycarbonylmethyl-3-carboxyperhydroazepine

Hydrogenate a solution of 1.0 g of this benzyl ester in 25 ml of 50% aqueous acetic acid using 10% palladium on carbon as catalyst. Filter and concentrate the filtrate *in vacuo* to obtain 1-methoxycarbonylmethyl-3-carboxyperhydroazepine.

D. 1-Methoxycarbonylmethyl-3-methylidenperhydroazepin-2-one

To a solution of 710 mg of this acid in 30 ml xylene, add 0.24 g $K_2CO_3$ and 510 mg acetic anhydride and reflux the stirred mixture for 5 hr. Cool the reaction to room temperature and pour it into a solution of 35 g $K_2CO_3$ in 70 ml $H_2O$ and stir at $-5°$ for 3 hr. Separate the layers, then dry and concentrate the xylene solution in vacuo. Chromatograph the crude product on silica gel using 1:1 ethyl acetate:hexane and isolate pure 1-methoxycarbonylmethyl-3-methylideneperhydroazepin-2-one.

NMR ($CDCl_3$, TMS) $\delta1.8$ (m, 4H); $\delta2.3$ (m, 2H); $\delta3.4$ (m, 2H); $\delta3.65$ (s, 3H); $\delta4.1$ (s, 2H); $\delta5.2$ (m, 1H); $\delta5.5$ (m, 1H).

E. 1-Methoxycarbonylmethyl-3-acetylmercaptomethylperhydroazepin-2-one

Dissolve 260 mg of this ester in 5 ml thiolacetic acid and store the solution at room temperature overnight. Concentrate the reaction and flush the residue with benzene in vacuo. Purify the 1-methoxycarbonylmethyl-3-acetylmercaptomethylperhydroazepin-2-one by silica gel chromatography. tlc: 2 ethyl acetate:3 hexane, silica gel. $R_f 0.5$ NMR ($CCL_4$, TMS) $\delta1.6$ (m, 6H); $\delta2.2$ (s, 3H); δ2.5–3.6 (m, 4H); δ3.6 (s, 3H); δ4.0 (2xd, J=17 hz, 2H).

Mass spectrum: M+ 273; m/e 230 (M+-CH₃CO); 198

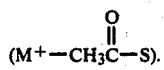
(M+—CH₃C—S).

F.
1-Carboxymethyl-3-mercaptomethylperhydroazepin-2-one

Hydrolyze under an atmosphere of nitrogen 200 mg of this diester in 6 ml H₂O and 5 ml CH₃OH made to pH 12 with NaOH. Acidify the hydrolysate to pH 2 and extract with ethyl acetate. Dry and concentrate the extracts to obtain 1-carboxymethyl-3-mercaptomethyl-perhydroazepin-2-one.

NMR: (CCl₄, TMS) δ1.7 (m, 8H); δ2.2–3.8 (m, 4H); δ4.2 (broad, 2×d, 2H). Mass spectrum: M+ 217; m/e 184 (M+—SH).

G.
1-Carboxymethyl-3-acetylmercaptomethylperhydroazepin-2-one

If desired, the mercapto-acid can be reacetylated in pyridine solution with slight excess of acetyl chloride to obtain the title compound.

EXAMPLE 2

A.
1-t-Butoxycarbonylmethyl-3,3-dibromoperhydroazepin-2-one

To a suspension of 300 mg of sodium hydride in 25 ml THF add a solution of 2.71 g of 3,3-dibromoperhydroazepin-2-one [R. Wineman et al., J. Am. Chem. Soc., 80, 6233 (1958)] and 2.50 g of t-butyl iodoacetate in 25 ml THF, carrying out the operation under N₂. Stir the reaction at room temperature for several hours, quench with aqueous NaHSO₃, isolate the organic phase, dry and concentrate in vacuo to obtain 1-t-butoxycarbonylmethyl-3,3-dibromoperhydroazepin-2-one.

B.
1-t-Butoxycarbonylmethyl-3-bromoperhydroazepin-2-one

Hydrogenate 1.93 g of this halide in 25 ml of ethanol containing 200 mg MgO using 10% palladium on charcoal as catalyst. Filter and concentrate the reaction mixture to obtain 1-t-butoxycarbonylmethyl-3-bromoperhydroazepin-2-one.

C.
1-t-Butoxycarbonylmethyl-3-methylideneperhydroazepin-2-one

Reflux a solution 3.05 g of this halide with 2.62 g triphenyl phosphine in 50 ml THF. Isolate the crude phosphonium salt, suspend it in H₂O and add dropwise 10% NaOH. Extract the mixture with chloroform, concentrate the extracts and isolate the desired ylid.

Reflux a suspension of 2.4 g of this ylid and 0.3 g paraformaldehyde in 75 ml THF under a nitrogen atmosphere. After 3 hours, cool the reaction and reduce the volume in vacuo. Add petroleum ether and pass the solution through a short silica gel column. Remove the solvent and isolate 1-t-butoxycarbonylmethyl-3-methylidene-perhydroazepin-2-one.

D. The product of C is converted to the desired mercapto acid as described in Example 1E and 1F and to the acetylmercapto acid, if desired, as described in Example 1G.

EXAMPLE 3

1-Carboxymethyl-3-mercaptomethyl-7-methylperhydroazepin-2-one

The procedure of Example 1A is followed, using an equivalent quantity of 3-carboxy-7-methylperhydrazepine [prepared from 3-hydroxy-6-methylpyridine by the procedures of Krogsgaard-Larsen, et al., Acta. Chem. Scand. B32, 327 (1978) and Ibid, B30, 884 (1976)] as the starting material. The procedures of parts B, C, D, E and F are then successively followed to produce 1-carboxymethyl-3-mercaptomethyl-7-methylperhydroazepin-2-one. If desired, the procedure of Example 1G can be followed to obtain 1-carboxymethyl-3-acetylmercaptomethyl-7-methylperhydroazepin-2-one.

EXAMPLE 4

1-(1-Carboxymethyl)-3-mercaptomethylperhydroazepin-2-one

When, in the procedure of Example 1B, an equivalent quantity of methyl α-bromoproprionate is used in place of methyl bromoacetate, there is obtained 1-(1-methoxycarbonylethyl)-3-benzyloxycarbonylperhydroazepin. When this is used in the successive procedures of parts C, D, E and F, there is obtained 1-(1-carboxyethyl)-3-mercaptomethylperhydroazepin-2-one.

EXAMPLE 5

R¹-Substituted Products as Formula I

By treatment with PBr₅ in benzene by the method of Nagasawa, et al. (J. Med. Chem. 14, 501 (1971)) the 7-substituted perhydroazepin-2-ones IX listed in Table I could be converted to the corresponding 7-substituted-3-bromo-perhydroazepin-2-ones. Treatment with t-butyl iodoacetate in tetrahydrofuran in the presence of sodium hydride in the manner of Example 2A could afford the corresponding 7-substituted-3-bromo-1-t-butoxycarbonylmethylperhydroazepin-2-one.

Treatment then with triphenylphosphine followed by paraformaldehyde as described in Example 2-C could afford the corresponding 7-substituted-1-t-butoxycarbonylmethyl-3-methylidene-perhydroazepin-2-one. Subsequent treatment with thiolacetic acid and hydrolysis as described in Examples 1-E and 1-F would yield the corresponding 7-substituted-1-carboxymethyl-3-mercaptomethylperhydroazepin-2-one.

The use of methyl α-bromopropionate as described in Example 4, followed by the steps of Example 2C, 1E, and 1F would produce the 7-substituted-1-carboxyethyl-3-mercaptomethylperhydroazepin-2-one. These 7-substituted-1-carboxyalkyl-3-mercaptomethylperhydroazepin-2-ones could, if desired, be converted to the corresponding 5-acyl derivative by treatment with an acylating agent, such as acetic anhydride or acetyl chloride, with pyridine or triethylamine.

TABLE I

| 7-Substituted Perhydroazepin-2-ones IX | | |
|---|---|---|
| R¹ | = | —C₂H₅ |
| | | -n-C₄H₉ |
| | | -cyclohexyl |

TABLE I-continued

7-Substituted Perhydroazepin-2-ones IX

-benzyl
-(1-piperidino)methyl
-p-tolyl
-p-anisyl
-p-chlorophenyl
-(2'-pyridyl)

[All of the above compounds are described in the chemical literature].

EXAMPLE 6

$R^1$-Aminoalkyl Substituted Products of Formula I

The known perhydroazepin-2-ones substituted in the 7-position by 2-aminoethyl or 4-aminobutyl groups could be converted to the corresponding phthalimido derivative at their primary amide functionality by known methods, and the resulting compounds treated as described in Example 5 to obtain compounds of Formula I where $R^1$ is the phthalimidoalkyl group, $R_2=H$, $R_3=$t-butoxy, and $R_4=CH_3CO$—. Careful hydrazinolysis would remove the phthalimide protecting group and further hydrolysis by standard methods would afford the desired mercapto acid I, where $R^1=(CH_2)_nNH_2$, where n=2 or 4, $R_2=H$, $R_3=OH$, and $R^4=H$. By employing methyl α-bromopropionate in place of iodoacetate the corresponding compounds I would be obtained in which $R_2=CH_3$.

EXAMPLE 7

Tablet Containing 25 mg of Active Ingredient

A typical tablet contains 1-carboxymethyl-3-mercaptomethylperhydroazepin-2-one (25 mg.), pregelatinized starch USP (82 mg.), microcrystalline cellulose (82 mg.) and magnesium stearate (1 mg.). In like manner, for example, 1-(1-carboxyethyl)-3-mercaptomethylperhydroazepin-2-one (20 mg.) may be formulated in place of 1-carboxymethyl-3-mercaptomethylperhydroazepin-2-one with the composition of pregelatinized starch, microcrystalline cellulose and magnesium stearate described above.

A combination tablet with a diuretic such as hydrochlorothiazide typically contains 1-carboxymethyl-3-mercaptomethylperhydroazepin-2-one (7.5 mg.), hydrochlorothiazide (50 mg.), pregelatinized starch USP (82 mg.), microcrystalline cellulose (82 mg.) and magnesium stearate (1 mg.). Tablets with, for example, 1-(1-carboxyethyl)-3-mercaptomethylperhydroazepin-2-one (5 mg.) and hydrochlorothiazide (50 mg.) are made by substituting the former in place of 1-carboxymethyl-3-mercaptomethylperhydroazepin-2-one in the composition described above.

EXAMPLE 8

Compressed Tablet Containing 50 mg. of Active Ingredient

| | Per tablet, Mg. |
|---|---|
| 1-Carboxymethyl-3-mercaptomethyl-perhydroazepin-2-one | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

EXAMPLE 9

Dry Filled Capsule Containing 50 mg. of Active Ingredient

| | Per capsule, Mg. |
|---|---|
| 1-Carboxymethyl-3-mercaptomethyl-perhydroazepin-2-one | 50 |
| Lactose | 273 |
| Magnesium stearate | 2 |
| Mixed powders | 325 |

Mix the active ingredient above, lactose, and magnesium stearate and reduce to a No. 60 mesh powder. Encapsulate, filling 325 mg. in each No. 2 capsule.

The above formulations can be employed to prepare compressed tablets or capsules of other novel compounds of this invention hereinbefore described.

The above examples describe the preparation of certain compounds which are illustrative of the novel compounds of this invention, and certain specific dosage forms suitable for administering the novel compounds. It is to be understood that the invention is not to be limited to the specific ingredients included in the pharmaceutical preparations, but is to be understood to embrace variations and modifications thereof which fall within the scope of one skilled in the art.

What is claimed is:

1. A compound of the formula:

$$R^4-S-CH_2-\underset{\underset{O}{\|}}{C}-N\underset{CH-COR^3}{\overset{R^1}{<}}$$
$$\qquad\qquad\qquad\qquad |$$
$$\qquad\qquad\qquad\qquad R^2$$

wherein:
$R^1$ is hydrogen, loweralkyl, unsubstituted cycloalkyl having 3 to 10 carbon atoms, amino loweralkyl, alkylamino loweralkyl, hydroxyalkyl, dialkylamino loweralkyl, arloweralkyl, aryl, substituted aryl wherein the substituent is halo, alkyl, aminoalkyl, or alkoxy;
$R^2$ is hydrogen or loweralkyl;
$R^3$ is hydroxyl, loweralkoxy, or aralkyloxy;
$R^4$ is hydrogen or loweralkanoyl; and,
the pharmaceutically acceptable salts thereof: wherein in said $R^1$, $R^2$, $R^3$ and $R^4$ groups, said alkyl groups have 1 to 12 carbon atoms; said loweralkyl groups have 1 to 8 carbon atoms; said aryl and said ar prefix denote unsubstituted aromatic ring(s) having 6 to 12 carbon atoms.

2. A compound of claim 1 in which

R¹ is hydrogen, loweralkyl, aminoloweralkyl, or aryl;

R² is hydrogen or loweralkyl;

R³ is hydroxyl, or loweralkoxy; and,

R⁴ is hydrogen or loweralkanoyl.

3. A compound of claim 2 which is 1-carboxymethyl-3-mercaptomethylperhydroazepin-2-one.

4. The compound of claim 2 which is 1-carboxymethyl-3-acetylmercaptomethylperhydroazepin-2-one.

5. A process for preparing compounds of the formula:

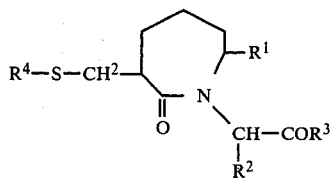
I wherein

R¹ is hydrogen, loweralkyl, unsubstituted cycloalkyl having 3 to 10 carbon atoms, amino loweralkyl, alkylamino loweralkyl, hydroxyalkyl, dialkylamino loweralkyl, arloweralkyl, aryl, substituted aryl wherein the substituent is halo, alkyl, aminoalkyl, or alkoxy;

R² is hydrogen or loweralkyl;

R³ is hydroxyl, loweralkoxy, or aralkyloxy;

R⁴ is hydrogen or loweralkanoyl, wherein in said R¹, R², R³ and R⁴ groups, said alkyl groups have 1 to 12 carbon atoms; said loweralkyl groups have 1 to 8 carbon atoms; said aryl and said ar prefix denote unsubstituted aromatic ring(s) having 6 to 12 carbon atoms which process comprises treating a compound having the structure:

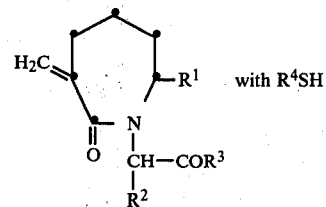 with R⁴SH wherein R¹, R² and R³ are as defined above and R⁴ is loweralkanoyl, followed by removal of protecting groups, if necessary, to yield the desired product and, if desired, isolating the biologically more active isomer by chromatography, fractional crystallization, or by resolution with an appropriate, optically active base and, if desired, preparing a salt of the desired product by conventional means.

6. The process of claim 5 wherein in the formula I compounds

R¹ is hydrogen, loweralkyl, aminoloweralkyl, or aryl;

R² is hydrogen or loweralkyl;

R³ is hydroxyl or loweralkoxy; and,

R⁴ is hydrogen or lower alkanoyl.

7. The compound:

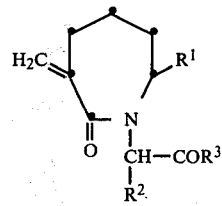

wherein R¹, R² and R³ are as defined in claim 1.

8. The compound:

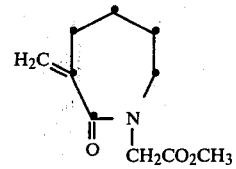

and the corresponding carboxylic acid thereof.

* * * * *

UNITED STATES PATENT AND TRADEMARK OFFICE
CERTIFICATE OF CORRECTION

PATENT NO. : 4,409,146
DATED : October 11, 1983
INVENTOR(S) : Thorsett, et al.

It is certified that error appears in the above—identified patent and that said Letters Patent is hereby corrected as shown below:

Column 12, Claim 1, in the formula, $R^4\text{-S-CH}^2$, should be -- $R^4\text{-S-CH}_2$ --

Column 13, Claim 5, in the formula, $R^4\text{-S-CH}^2$, should be -- $R^4\text{-S-CH}_2$ --

Signed and Sealed this

Thirteenth Day of December 1983

[SEAL]

Attest:

GERALD J. MOSSINGHOFF

Attesting Officer

Commissioner of Patents and Trademarks